United States Patent
van Broekhoven et al.

(10) Patent No.: US 11,225,614 B2
(45) Date of Patent: Jan. 18, 2022

(54) ALKYLATION PROCESS WITH IMPROVED OCTANE NUMBER

(71) Applicants: Emanuel Hermanus van Broekhoven, Monnickendam (NL); Ruben Theodoor Pronk, Jisp (NL); Jackeline Medina, The Woodlands, TX (US)

(72) Inventors: Emanuel Hermanus van Broekhoven, Monnickendam (NL); Ruben Theodoor Pronk, Jisp (NL); Jackeline Medina, The Woodlands, TX (US)

(*) Notice: Subject to any disclaimer, the term of this patent is extended or adjusted under 35 U.S.C. 154(b) by 0 days.

(21) Appl. No.: 16/490,644

(22) PCT Filed: Mar. 1, 2018

(86) PCT No.: PCT/EP2018/055063
§ 371 (c)(1),
(2) Date: Sep. 3, 2019

(87) PCT Pub. No.: WO2018/158377
PCT Pub. Date: Sep. 7, 2018

(65) Prior Publication Data
US 2020/0002624 A1 Jan. 2, 2020
US 2021/0371758 A9 Dec. 2, 2021

Related U.S. Application Data

(60) Provisional application No. 62/465,535, filed on Mar. 1, 2017.

(51) Int. Cl.
*C10G 29/20* (2006.01)
*C07C 2/58* (2006.01)
*C10G 7/02* (2006.01)

(52) U.S. Cl.
CPC ............. *C10G 29/205* (2013.01); *C07C 2/58* (2013.01); *C10G 7/02* (2013.01); *C10G 2300/1081* (2013.01); *C10G 2300/1088* (2013.01); *C10G 2400/02* (2013.01); *C10G 2400/04* (2013.01); *C10G 2400/08* (2013.01)

(58) Field of Classification Search
CPC ........ C10G 29/20; C10G 29/205; C07C 2/58; C07C 2/62
See application file for complete search history.

(56) References Cited

U.S. PATENT DOCUMENTS

| | | |
|---|---|---|
| 3,644,565 A | 2/1972 | Biale |
| 3,851,004 A | 11/1974 | Yang |
| 4,404,418 A | 9/1983 | Huston, Jr. et al. |
| 4,456,779 A | 6/1984 | Hartley et al. |
| 5,986,158 A | 11/1999 | Van Broekhoven et al. |
| 7,176,340 B2 | 2/2007 | Van Broekhoven et al. |
| 7,750,197 B2 | 7/2010 | Van Broekhoven et al. |
| 8,163,969 B2 | 4/2012 | Van Broekhoven et al. |
| 8,487,154 B2 | 7/2013 | Timken et al. |
| 2002/0198422 A1 | 12/2002 | Van Broekhoven et al. |
| 2006/0194998 A1 | 8/2006 | Umansky et al. |
| 2007/0293390 A1 | 12/2007 | Van Broekhoven et al. |
| 2010/0234661 A1 | 9/2010 | Van Broekhoven et al. |
| 2011/0313227 A1 | 12/2011 | Van Broekhoven et al. |
| 2017/0369395 A1* | 12/2017 | Dakka .................. B01J 37/0018 |

FOREIGN PATENT DOCUMENTS

| | | |
|---|---|---|
| EA | 11022 B1 | 12/2008 |
| EP | 1714952 | 10/2006 |
| RU | 2313391 C2 | 12/2007 |
| WO | WO1998023560 | 6/1998 |
| WO | WO2014109766 | 7/2014 |
| WO | WO2016005391 | 1/2016 |
| WO | WO2016210006 | 12/2016 |

OTHER PUBLICATIONS

Corma, A., et al., "Chemistry, Catalysts, and Processes for Isoparaffin-Olefin Alkylation: Actual Situation and Future Trends" Catalysis Reviews Science and Engineering, 35(4) (1993), p. 503.

* cited by examiner

*Primary Examiner* — Renee Robinson
(74) *Attorney, Agent, or Firm* — Nathaniel C. Dunn; Marcy M. Hoefling; Troy S. Kleckley

(57) ABSTRACT

An improved alkylation process with improved octane number and lower final boiling point. Further, the present disclosure comprises an alkylation system that allows flexibility in the operating parameters without loss of productivity. This enhances the advantage of the solid acid alkylation process of the invention over the liquid acid processes, as the C9+ alkylate will mainly contain the desired highly branched paraffin's in the case of solid acid alkylation. By fractionation of C9+, the RON number of the gasoline alkylate after fractionation remains very high, while the final boiling point of the gasoline fraction will decrease, improving value and blending flexibility.

21 Claims, No Drawings

ALKYLATION PROCESS WITH IMPROVED OCTANE NUMBER

BACKGROUND OF THE INVENTION

The present invention relates to a process for alkylating a hydrocarbon feed which comprises contacting the hydrocarbon feed to be alkylated with an alkylation agent in the presence of a catalyst comprising a solid acid and a hydrogenation function, e.g. a hydrogenation metal.

The term alkylation refers to the reaction of an alkylatable compound, such as a saturated hydrocarbon, with an alkylation agent, such as an olefin. The reaction is of interest because it makes it possible to obtain, through the alkylation of isoparaffins such as isobutane with an olefin containing 2-6 carbon atoms, an alkylate which has a high octane number and which boils in the gasoline range. Unlike gasoline obtained by cracking heavier petroleum fractions such as vacuum gas oil and atmospheric residue, gasoline obtained by alkylation is essentially free of contaminants such as sulfur and nitrogen and thus has clean burning characteristics. Its high anti-knock properties, represented by the high octane number, lessen the need to add environmentally harmful anti-knock compounds such as aromatics or lead. Also, unlike gasoline obtained by reforming naphtha or by cracking heavier petroleum fractions, alkylate contains few if any aromatics or olefins, which offers further environmental advantages.

The alkylation reaction is acid-catalyzed. Conventional alkylation process equipment makes use of liquid acid catalysts such as sulfuric acid and hydrofluoric acid. The use of such liquid acid catalysts is attended with a wide range of problems. For instance, sulfuric acid and hydrofluoric acid are both highly corrosive, so that the equipment used has to meet severe service requirements. Since the presence of highly corrosive materials in the resulting fuel is objectionable, the remaining acid must be removed from the alkylate. Also, because of the liquid phase separations that must be carried out, the process is complicated and expensive. In addition, there is always the risk that toxic substances such as hydrogen fluoride will be emitted to the environment.

A problem that is encountered in the case of gasoline alkylation processes is that, when more severe process conditions are applied, e.g. by increasing the space velocity of olefins (olefin whsv) and/or reducing the isoparaffin over olefins ratio (I/O) in the feed, the C9+ heavier hydrocarbon fraction (boiling point above about 150° C.) in the product C5+ alkylate increases. This leads to both a higher final boiling point (FBP) and a lower octane number (RON) of the C5+ alkylate fraction produced. Lower octane since the heavier C9+ fraction has a blending octane contribution of about 84, while the C5+ to C8 fraction has a blending RON contribution which is about 12-15 points higher (abt. 96-99).

Lower RON and higher FBP are unfavorable with regard to the value of alkylate as a gasoline blending component. However, by separation by e.g. distillation (or any other suitable method) the C9+ fraction can be removed from alkylate, thereby reducing the FBP and increasing the octane number depending on the severity. The higher the severity the more C9+ is formed and the higher the octane improvement and FBP reduction after separation of C9+.

C9+ is mainly composed of highly branched high purity paraffins and may be used for kerosene/jet fuel. It should be noted that this highly branched C9+ alkylate fraction contains no olefin, naphthenic and aromatic compounds and for this reason burns clean without "sooth" formation. For this reason the co-production of this high quality C9+ fraction next to alkylate can be an attractive option for refineries.

A problem encountered in the case of liquid acid (HF and H2SO4) processes is that the amount of acid soluble oil (ASO) side products increases at higher severity and ASO is a waste product that needs to be removed and burned. Also the ASO concentration has a strong effect on the activity and selectivity of the liquid acid processes and should be strictly controlled to get optimum performance (reference U.S. Pat. No. 4,404,418 for HF and for H2SO4 A. Corma and A. Martinez, "Chemistry, Catalysts, and Processes for Isoparaffin-Olefin Alkylation: Actual Situation and Future Trends", Catal. Rev.-Sci. Eng., 35(4), 483-570 (1993), page 503). This limits the flexibility of the liquid acid processes to co-produce the C9+ fraction strongly.

Other prior art describes the use of distillation of kerosene, jet fractions and heavy distillates from alkylate, U.S. Pat. No. 8,487,154 ("Market driven alkylation or oligomerization process" to Timken, et al.) In this case ionic liquids are used as catalysts and it can be expected these fractions potentially will contain halogens and nitrogen from the ionic liquids. Also next to the desirable light distillate, also less desirable heavy distillate is formed in similar quantities. Solid acid alkylation by zeolites as we use will not lead to the presence of S, halogens and nitrogen compounds. These compounds need to be removed from HF, H2SO4 and ionic liquid acid alkylation products. In case of all liquid acid processes (HF, H2SO4, ionic liquids) the presence of ASO (acid soluble oil, conjunct polymers, red oil) has a strong impact on product distribution and properties of alkylate (e.g. RON of the gasoline fraction).

However, in the case of solid acid alkylation (SAC) processes of the invention no ASO is formed and consequently the limits for co-production of C9+ are relaxed. Also by the absence of the use of HF or $H_2SO_4$, little to no halogen, and sulphur impurities will be present. This could make the C9+ fraction of the solid acid alkylation process not only useful as jet fuel blending component but potentially also for the production of a niche fuel for rockets that otherwise only can be obtained by intense purification.

Historically the activity and stability of solid acid alkylation catalysts have left much still to be desired when compared to competitive liquid acid alkylation processes. Recent developments in solid acid alkylation have included alkylation processes employing the facile regeneration of zeolite-containing solid acid catalysts by gas mixtures comprising hydrogen at 200-300° C. (HTR) and combinations of HTR and milder regeneration with dissolved hydrogen (LTR), as disclosed in U.S. Pat. No. 5,986,158 ("Process for alkylating hydrocarbons" to Van Broekhoven, et al), improved solid acid catalyst production processes as per US Patent Application Publication 2007/0293390 ("Alkylation Catalyst, Its Preparation and Use" to Van Broekhoven, et al), alkylation catalyst hydration processes as per U.S. Pat. No. 7,750,197 ("Alkylation process using a catalyst comprising a solid acid and a hydrogenation metal" to Van Broekhoven, et al), continuous or semi-continuous alkylation and regeneration processes as per U.S. Pat. No. 7,176,340 ("Continuous process for the alkylation of hydrocarbons" to Van Broekhoven, et al), US 2002/198422 ("Process for the catalytic alkylation of hydrocarbons" to Broekhoven, et al).

Another historical attempt at creating an active and stable solid acid alkylation catalyst includes U.S. Pat. No. 3,851, 004 ("Hydrocarbon alkylation process using catalyst regeneration"). The '004 reference relates to a process for the alkylation of hydrocarbons using zeolite-containing catalysts and more particularly to aromatic or isoparaffin alkylation processes wherein the reaction is catalysed by a zeolitic molecular sieve catalyst in conjunction with a group VIII metal hydrogenation agent. However, the '004 reference specifically teaches that the addition of rare earth cations is not essential.

Other prior art attempts at creating an active and stable solid acid alkylation catalyst include U.S. Pat. No. 8,163,969 ("Alkylation process using a catalyst comprising rare earth containing zeolites and a hydrogenation metal" to Van Broekhoven, et al.), U.S. Patent Application Publication 2010/0234661 ("Alkylation process using a catalyst comprising rare earth containing zeolites and reduced amount of noble metal" to to Van Broekhoven, et al.), U.S. Patent Application Publication 2011/0313227 ("Alkylation catalyst and related process" to Van Broekhoven, et al), and WO 2016/005391 ("Alkylation process using a catalyst comprising cerium rich rare earth containing zeolites and a hydrogenation metal" to Van Broekhoven, et al). These references are herein incorporated by reference. These prior at tempts disclose rare earth exchanged molecular sieves (e.g., Y-zeolites) in such solid acid alkylation catalysts.

Another example of a SAC process recently published is WO2016/210006 ("Improved catalyzed alkylation, alkylation catalysts, and methods of making alkylation catalysts" to Mukherjee, et al.) This application discloses an alkylation method that comprises reaction over a solid acid, zeolite-based catalyst and further amongst others having a characteristic catalyst life property. The alkylation catalyst comprises a crystalline zeolite structure, a Si/Al molar ratio of 20 or less, less than 0.5 weight percent alkali metals, and further having a characteristic catalyst life property. Some catalysts may contain rare earth elements in the range of 10 to 35 wt %. However, this process uses HTR only.

In the case of rocket fuel, specifications are even stricter, allowing no halogen, sulfur and nitrogen impurities in order to prevent corrosion issues. This enhances the advantage of the solid acid alkylation process of the invention over the liquid acid processes, next to that the C9+ alkylate will mainly contain the desired highly branched paraffin's in the case of solid acid alkylation. Another technical problem solved by the process of the invention using fractionation of C9+ is that the RON number of the gasoline alkylate after fractionation remains very high, while the final boiling point of the gasoline fraction will decrease, improving value and blending flexibility.

Thus there remains a need for an alkylation system that allows flexibility in the operating parameters without loss of productivity. Further, there remains a need for a stable and active solid acid alkylation process with improved octane number and lower final boiling point yielding maximum clean kerosene.

BRIEF DESCRIPTION OF THE INVENTION

The use of the SAC process of the invention allows the production of a high purity kerosene fraction without the large impact on e.g. RON of the gasoline fraction. Also no waste ASO is formed and the product is free from S, N, halogens, aromatics and olefins. The process uses higher olefin space velocities (e.g. whsv of the olefin from 100% to 150% of the whsv for gasoline production only), lower isoparaffin over olefin ratio I/O of combined olefin feed and isoparaffin recycle (=I/O external e.g. from 50% to 100% of I/O external for gasoline production only), lower I/O in the feed at the inlet to the catalyst beds (=I/O internal e.g. of 50% to 100% of I/O internal for gasoline production only), separately or combinations thereof. Furthermore by using the differing conditions mentioned above it may be required to optimize the reactor temperature within −20% to +20% of the temperature required for the gasoline only mode of operation. After separation the gasoline fraction will still have a very high RON (e.g. higher than 94, preferably 95, more preferably 96), no N, no S, no halogen. Only a light distillate kerosene fraction of high purity is produced and essentially no heavy distillates.

In other embodiments when using the process with a low temperature regeneration reactor with dissolved hydrogen (see, e.g., U.S. Pat. No. 5,986,158) also no olefins will be present in the alkylation products. In case of ionic liquids (U.S. Pat. No. 8,487,154) the use of a hydro finishing reactor is required to remove olefins from gasoline and heavier fractions by hydrogenation.

In summary the new SAC process of the invention allows the co-production of valuable light distillate kerosene/jet fuel next to high quality alkylation gasoline without the co-production of ASO waste and/or low value heavy distillate. The new process allows the use of much more severe process conditions, e.g. much higher olefin whsv, lower I/O external and internal. This results in much lower operation costs per unit of product of the new SAC process. Surprisingly, the quality of the co-produced alkylation gasoline fraction remains very high.

DETAILED DESCRIPTION OF THE INVENTION

All weight percentages mentioned related to the catalyst composition are based on dry catalyst (heated at 600° C. for 1 hour). The rare earth wt % are calculated as rare earth oxides on a dry basis (600° C., 1 hour). It should further be understood that, when describing steps or components or elements as being preferred in some manner herein, they are preferred as of the initial date of this disclosure, and that such preference(s) could of course vary depending upon a given circumstance or future development in the art.

The Alkylation Process

The present invention describes a process for alkylating hydrocarbons wherein an alkylatable organic compound is reacted with an alkylation agent to form an alkylate in the presence of a catalyst, wherein said catalyst comprises a hydrogenating function and a solid acid constituent, wherein the feed is processed using process conditions that lead to a higher quantity of a C9+ product fraction formed than process conditions optimized for gasoline production. In one embodiment, the present invention relates to a process for alkylating a hydrocarbon feed which comprises contacting the hydrocarbon feed to be alkylated with an alkylation agent in the presence of a catalyst comprising a solid acid and a hydrogenation metal. Preferably, the hydrocarbon to be alkylated in the alkylation process is a branched saturated hydrocarbon such as an isoalkane having 4-10 carbon atoms. Examples are isobutane, isopentane, isohexane or mixtures thereof, with isobutane being most preferred. The alkylation agent preferably is an olefin having 2-10 carbon atoms, more preferably 2-6 carbon atoms, still more preferably 3-5 carbon atoms, and most preferably 4 carbon atoms. Most preferably, the alkylation process consists of the alkylation of isobutane with butenes.

As will be evident to the skilled person, the alkylation process can take any suitable form, including fluidized bed processes, slurry processes, and fixed bed processes. The process can be carried out in a number of beds and/or reactors, each with separate addition of alkylation agent if desirable. In such a case, the process of the invention can be carried out in each separate bed or reactor. It may be necessary after the initial run to further distil the product. Distillation can occur by methods known in the art.

Suitable process conditions are known to the skilled person. In case of SAC alkylation frequent regeneration with $H_2$ is required. This can comprise a higher temperature re-generation with a gas that comprises $H_2$ (HTR) and/or mild regeneration with hydrocarbons that comprise dissolved $H_2$ (LTR). Preferably, an alkylation process as disclosed in WO 98/23560 is applied.

However, the process of the current invention prefers the use of higher olefin space velocities (whsv olefin from 100% to 150% of whsv for gasoline production only), lower I/O of combined olefin feed and isoparaffin e.g. isobutane recycle (=I/O external from 50% to 100% of I/O external for gasoline production only), lower I/O in the feed at the inlet to the catalyst beds (=I/O internal of 50% to 100% of I/O internal for gasoline production only), separately or combinations thereof. Therefore, one embodiment of the current invention is an alkylation process that is operated with olefin space velocities greater than 110% and/or I/O external and/or I/O internal of lower than 90% of used for the conventional gasoline alkylation process. More preferably olefin whsv of greater than 115% and/or I/O external and/or I/O internal of lower than 85% of used for the conventional gasoline alkylation process. The process of the current invention is characterized in that after separation the gasoline fraction will still have a very high RON (e.g. higher than 94, preferably higher than 95, most preferably higher than 96), no N, no S, no halogen. Only a light distillate kerosene/jet fuel fraction of high purity is co-produced and essentially no heavy distillates. The quantity of co-produced C9+ kerosene and jet fuel is generally higher than 5%, preferably higher than 10% and most preferably higher than 15% of the gasoline alkylate quantity produced.

The Catalyst

A suitable catalyst is described in Patent Application WO 2016/005391, which is incorporated herein. More specifically, the catalyst comprises a solid acid. Examples of solid acids are zeolites such as zeolite beta, MCM-22, MCM-36, mordenite, faujasites such as X-zeolites and Y-zeolites, including H-Y-zeolites and USY-zeolites, non-zeolitic solid acids such as silica-alumina, sulfated oxides such as sulfated oxides of zirconium, titanium, or tin, mixed oxides of zirconium, molybdenum, tungsten, phosphorus, etc., and chlorinated aluminium oxides or clays. Preferred solid acids are zeolites, including mordenite, zeolite beta, faujasites such as X-zeolites and Y-zeolites, including HY-zeolites and USY-zeolites. Mixtures of solid acids can also be employed. In one embodiment the solid acid is a faujasite with a unit cell size ($a_0$) of 24.72 to about 25.00 angstroms, in another embodiment the solid acid is Y-zeolite with a unit cell size of 24.34-24.72 angstroms, while in another the solid acid is Y-zeolite with a unit cell size of 24.42-24.56 angstroms. In yet another embodiment the solid acid is Y-zeolite with a unit cell size of 24.56-24.72 angstroms.

The catalyst further comprises a hydrogenation function, preferably a hydrogenation metal. Examples of suitable hydrogenation metals are the transition metals, such as metals of Group VIII of the Periodic Table, and mixtures thereof. Among these, noble metals of Group VIII of the Periodic Table are preferred. Platinum, palladium, and mixtures thereof are especially preferred. The amount of hydrogenation metal will depend on its nature. When the hydrogenation metal is a noble metal of Group VIII of the Periodic Table, the catalyst generally will contain in the range of about 0.01 to about 2 wt % of the metal. In one embodiment it ranges from about 0.1 to about 1 wt %, calculated as metal and based on the total weight of the catalyst.

In some embodiments the catalyst contains water. The water content of the catalyst ranges from about 1.5 wt % to about 6 wt %, in one embodiment it ranges from about 1.8 wt % to about 4 wt %, and in another embodiment it ranges from about 2 wt % to about 3 wt %. The water content of the catalyst is defined as its water content during use in the alkylation process and is measured by determining the water loss upon heating the catalyst to 600° C. including two hours at 600° C. (LOI 600).

The catalyst may comprise rare earth, i.e., an element chosen from the lanthanide series or combinations of such elements. In one embodiment, the solid acid component of the catalyst comprises from about 0.5 wt % to about 32 wt % rare earth. In another, the solid acid component of the catalyst comprises from about 2 wt % to about 9 wt % rare earth. In yet another, the solid acid component of the catalyst comprises from about 4 wt % to about 6 wt % rare earth.

Preferably, at least a portion of the rare earth element component of the catalyst is cerium. The amount of cerium in the final catalyst preferably is more than 0.1 wt %. More preferably, the cerium content is at least 0.3 wt %. Most preferably, the cerium content is at least 0.5%. The rare earth element(s) may be exchanged into the solid acid component by conventional means. In one embodiment, the rare earth element of the solid acid component is substantially all cerium. In another embodiment, the rare earth element of the solid acid component is a cerium rich rare earth mixture. In this mixture, the amount of cerium preferably is more than 3 wt % of the mixture. More preferably, the cerium content is more than 5 wt % of the mixture. Most preferably, the cerium content is at least 10% of the mixture. The balance of the rare earth mixture would substantially comprise one or more other rare earth elements, i.e., an element chosen from the lanthanide series, such as lanthanum, or combinations of such elements.

In other embodiments, additional cerium is added to the catalyst. This is performed by impregnation and/or ion exchange of the solid acid-containing particles. For example, this process can be carried out by pore volume impregnation using a cerium nitrate or cerium chloride solution and about 95-115 wt %, preferably 105 wt % saturation level compared to the water pore volume of the catalyst. Followed, by calcination at about 380-550° C., preferably 420-500° C. Preferably, the catalyst is dried, preferably at about 110-150° C., more preferably 120-130° C., before calcination. Alternatively, the catalyst particles may be exchanged with the cerium solution and dried and calcined at similar conditions as used after impregnation. Preferably, ion exchange and/or impregnation with cerium are carried out before addition of the group VIII metal(s) to the catalyst.

During the exchange process of the solid acid component, sodium (Na+) is removed from the catalyst. In one embodiment the solid acid component contains less than 2.0 wt % $Na_2O$. In another, less than 1.5 wt % $Na_2O$. In yet another less than 1 wt % $Na_2O$, also potentially less than 0.6 wt % $Na_2O$, all calculated on dry basis (600° C., 1 hour).

The catalyst may additionally comprise a matrix material. Examples of suitable matrix materials are alumina, silica, titania, zirconia, clays, and mixtures thereof. Matrix materials comprising alumina are generally preferred. In one embodiment, the catalyst comprises about 2 wt % to about 98 wt % of the solid acid and about 98 wt % to about 2 wt % of the matrix material, based on the total weight of the solid acid and the matrix material present in the catalyst. In another embodiment, the catalyst comprises about 10 wt % to about 90 wt % of the solid acid and about 90 wt % to about 10 wt % of the matrix material, based on the total weight of the solid acid and the matrix material contained in the catalyst. In another embodiment, the catalyst comprises about 10 wt % to about 80 wt % of matrix material and balance solid acid. In yet another embodiment, the catalyst comprises about 10 wt % to about 40 wt % of the matrix material and balance solid acid, based on the total weight of the solid acid and the matrix material contained in the catalyst.

The catalyst preferably contains less than 0.5 wt % of halogens. More preferably the catalyst contains no more than trace amounts of halogens.

The pore volume for pores less than 100 nm in diameter, as well as the total pore volume of produced catalysts were determined via mercury (Hg) intrusion on the basis of the Washburn equation $$D = \frac{-4\gamma\cos\theta}{p}$$

with D being the pore diameter, p being the pressure applied during the measurement, γ being the surface tension, taken to be 480 dynes/cm, and θ being the contact angle, taken to be 140°. In the present measurement, the pressure was varied over such a range that the measurement covered pores with a diameter in the range of 4.2-8000 nm.

In one embodiment, the catalyst has a total pore volume of at least about 0.23 ml/g and in another at least about 0.25 ml/g. More preferably, the total pore volume is at least 0.3 ml/g and most preferably at least 0.4 ml/g.

The particles of the catalyst can have many different shapes, including spheres, cylinders, rings, and symmetric or asymmetric polylobes, for instance tri- and quadrulobes.

In one embodiment, the catalyst particles have an average particle diameter of at least about 0.5 mm, in another embodiment at least about 0.8 mm, and in yet another embodiment at least about 1.0 mm. In one embodiment, the upper limit of the average particle diameter lies at about 10.0 mm, in another at about 5.0 mm, and in yet another embodiment at about 3.0 mm.

Preferably, the catalyst comprises, or essentially consists of, a hydrogenation metal, a cerium rich rare earth exchanged molecular sieve and, optionally, a matrix material. More preferably, the catalyst comprises, or essentially consists of, one or more cerium rich rare earth exchanged faujasite(s), one or more Group VIII metal(s), and one or more matrix material(s). Even more preferably, the catalyst of the invention comprises, or essentially consists of, one or more Group VIII noble metal compounds, one or more cerium rich rare earth exchanged Y-zeolites, and one or more matrices comprising alumina.

The catalyst can be prepared by processes now known to the industry, modified to achieve the particular pore characteristics of this invention. A typical process comprises the successive steps of
(i) shaping, e.g., extruding the solid acid constituent, optionally after mixing it with a matrix material, to form particles,
(ii) calcining the resulting particles, and
(iii) incorporating the hydrogenation metal into the calcined particles by, e.g., impregnating the particles with a solution of a hydrogenation metal component and/or by (competitive) ion exchange.

Alternatively, the catalyst can, e.g., be prepared by a process comprising the successive steps of
(i) incorporating the hydrogenation metal into the solid acid constituent or into a mixture of the solid acid constituent and the matrix material,
(ii) shaping, e.g., extruding the resulting material to form particles, and
(iii) calcining the resulting particles.

With regard to catalyst preparation, the procedures described in U.S. Pat. No. 8,163,969 also can be followed. In order to obtain the particular porosity characteristics of the present invention, it is particularly useful to carry out the extrusion step carefully. Thus, it is particularly useful to carry out the extrusion as follows:
1) mixing the matrix material (e.g., precipitated alumina powder), rare earth-exchanged molecular sieve (e.g., zeolite), water, nitric acid and a few percent of an extrusion aid (e.g. methylcellulose) to form a mixture,
2) feeding this mixture to an extruder, and
3) depending on visual inspection of the resulting extrusion product, adding some extra water during extrusion.

In carrying out this procedure experimentally to obtain catalysts of the invention, it was observed that water content (LOI 600) of the final extrusion mixture was in the order of 45 to 55 wt %. In the order of 0.05 to 0.25 equivalent (relative to the alumina powder) of nitric acid was added. Zeolite content of the extrudates was in the order of 65 to 85 wt % and the balance matrix and hydrogenation metal (0.05 to 1 wt %), calculated on dry basis (600° C., 1 hour). Those skilled in the art can now appreciate that the exact water content and acid addition required to get the extrudates with the desired properties (including physical strength such as side crushing strength and bulk crushing strength) depend on the molecular sieve content and the specific properties of the matrix material used. This is typically found by trial and error experiments after the starting component materials have been determined. The average particle length ranges from about 1 to about 6 mm, the particle diameter ranges from about 0.5 to about 3 mm, and the side crushing strength ranges from about 1 to about 10 lbs/mm.

The catalyst is particularly suitable for the alkylation of saturated hydrocarbons. The invention therefore further pertains to the use of the catalyst of the invention in the alkylation of these feed stocks. As stated above, this comprises the reaction of a saturated hydro-carbon with an olefin or olefin precursor in the presence of the catalyst of the invention to give highly branched saturated hydrocarbons with a higher molecular weight.

As mentioned above, water may be added during the process in order to increase the water content of the catalyst to the desired level. This water can be introduced during the alkylation reaction via, e.g., the hydrocarbon feed or the feed of alkylation agent. Alternatively, the catalyst can be hydrated by using a water-containing atmosphere during the optional (mild) regeneration steps described below, or by contacting the catalyst with water in a separate intermediate hydration step. Similar procedures can be applied to rehydrate the catalyst after its water content has decreased during processing (i.e. during the alkylation reaction and/or regeneration).

In one embodiment the catalyst used in the process according to the invention is prepared by adjusting the water content. For example, the solid acid constituent may be mixed with a matrix material, to form carrier particles, followed by calcination of the particles. The hydrogenating function may, e.g., be incorporated into the catalyst composition by impregnating the carrier particles with a solution of a hydrogenation metal component. After impregnation the catalyst may be calcined.

In one embodiment, the catalyst is reduced at a temperature of at least 150° C. In another embodiment, the catalyst is reduced at a temperature in the range of about 200 to about 600° C. in a reducing gas such as hydrogen. In yet another embodiment, the catalyst is reduced at a temperature in the range of about 250 to about 350° C. The reduction can be performed before adjustment of the water content, after addition of water to the catalyst and/or by using reduction as a way to adjust the water content. In one embodiment, the reduction is performed before adjustment of the water content. In another, the reduction is performed after drying the catalyst in a dry, non-reducing gas (such as nitrogen, helium, air, and the like).

The water content of the catalyst can be adjusted by various methods as described in U.S. Pat. No. 7,750,197 which is incorporated by reference in its entirety. Such methods are exemplified below as methods 1, 2, and 3.

Method 1 involves increasing the water content of a catalyst by exposing the catalyst to water. This can be achieved by exposing the catalyst to a water-containing atmosphere, e.g., air at ambient conditions. Embodiments of this method include exposing a reduced catalyst to water until the desired water content is reached, exposing an unreduced catalyst to water until a water content above the desired level is reached, followed by reduction of the catalyst, thereby decreasing the water content to the desired level, exposing a reduced catalyst to water until a water content above the desired level is reached, followed by treatment of the catalyst in either an inert or a reducing atmosphere, thereby decreasing the water content to the desired level, and reducing the catalyst in a hydrogen and water-containing atmosphere.

Method 2 involves decreasing the water content of an existing catalyst to the desired level by reducing an unreduced catalyst with water content above the desired level.

Method 3 involves in-situ water addition by starting the alkylation process with a catalyst having a water content below the desired level and adding water to the alkylation unit during processing, for instance by adding water to the hydrocarbon feed, by regenerating the catalyst in a water-containing atmosphere and/or by exposing the regenerated catalyst to a water-containing atmosphere.

A combination of two or more of the above methods may also be employed.

Optionally, the catalyst may be subjected to high-temperature regeneration with hydrogen in the gas phase. This high-temperature regeneration may be carried out at a temperature of at least about 150° C., in one embodiment regeneration is carried out at about 150° to about 600° C., and another at about 200° to about 400° C. For details of this regeneration procedure, reference is made to U.S. Pat. No. 5,986,158 and in particular to Col 3, ll 4-19, which is herein incorporated in its entirety by reference. The high-temperature regeneration can be applied periodically during the alkylation process. If as a result of high-temperature regeneration the water content of the catalyst has decreased to below the desired level, the catalyst may be rehydrated during the process in the ways described above.

In addition to the high-temperature regeneration treatment, a milder regeneration may be applied during the alkylation process, such as described in WO 98/23560, in particular page 9, line 13 through page 13, line 2, which is herein incorporated by reference in its entirety. During the alkylation process, the catalyst may be subjected intermittently to a regeneration step by being contacted with a feed containing a hydrocarbon and hydrogen, with said regeneration being carried out at about 90% or less of the active cycle of the catalyst in one embodiment, at 60% or less in another embodiment, at 20% or less in yet another embodiment, and at 10% or less in another embodiment. The active cycle of the catalyst is defined herein as the time from the start of the feeding of the alkylation agent to the moment when, in comparison with the alkylation agent added to the catalyst-containing reactor section, 40% of the alkylation agent leaves the catalyst-containing reactor section without being converted, not counting isomerization inside the molecule.

In one embodiment, the preparation of a catalyst of the present invention can comprise the steps of: a) calcining solid acid-containing particles at a temperature in the range of about 400 to about 575° C.; b) incorporating a Group VIII preferably noble metal into the calcined particles to form metal-containing particles; and c) calcining the metal-containing particles at a temperature in the range of about 350 to about 600° C. Alternatively, after a), additional cerium can be added to the catalyst by ion exchange and/or impregnation followed by drying and/or calcination. Thereafter, the metal is added.

Performance in alkylation reactions of catalysts of the present invention can be further improved if the calcination steps before and after incorporation of cerium and after the incorporation of hydrogenation component are conducted in a specific temperature window.

The solid acid-containing particles are calcined in step a) at a temperature in the range of about 400 to about 575° C., in another embodiment in the range of about 450 to about 550° C., and in yet another embodiment in the range of about 460 to about 500° C. The heating rate ranges from about 0.1 to about 100° C./min, and in one embodiment from about 0.5° C. to about 50° C./min, and in another embodiment from about 1 to about 30° C./min. Calcination is conducted for about 0.01 to about 10 hrs, and in one embodiment for about 0.1 to about 5 hrs, and in another embodiment for about 0.5 to about 2 hrs. It may be conducted in an air and/or inert gas (e.g. nitrogen) flow. In one embodiment this gas flow is dry.

In another embodiment, the solid acid-containing particles are dried before being calcined. This drying may be conducted at a temperature of about 110 to about 150° C.

The calcination can be performed in any equipment, such as a fixed bed reactor, a fluidized bed calciner, and a rotating tube calciner.

A Group VIII metal is then incorporated into the calcined solid acid-containing particles in step b). In one embodiment, this is performed by impregnation or competitive ion exchange of the solid acid-containing particles using a solution comprising Group VIII metal ions and/or their complexes and (optionally) NH4+ ions. In another embodiment, the Group VIII metals are platinum, palladium, and combinations thereof. In yet another embodiment, the Group VIII noble metal is platinum. Suitable Group VIII metal salts include nitrates, chlorides, and ammonium nitrates of the (noble) metals or their complexes (e.g. NH3 complexes).

The resulting metal-containing particles are then calcined at a temperature in the range of 350-600° C. in step c). In one embodiment, the particles are calcined at about 400 to about 550° C., and in another from about 450 to about 500° C. This temperature may be reached by heating the particles by about 0.1 to about 100° C./min to the desired final value between about 350 and about 600° C. In one embodiment, they are heated by about 0.5 to about 50° C./min, in another by about 1 to about 30° C./min. Calcination may be conducted for about 0.01 to about 10 hrs, and in one embodiment for about 0.1 to about 5 hrs, and in another for about 0.5 to about 2 hrs. Calcination of metal containing particles preferably is conducted in an air and/or oxygen containing gas flow. In one embodiment this gas flow is dry.

Optionally, a separate drying step is applied between steps (b) and (c). Alternatively, the metal-containing particles are dried during the calcination step. Also optionally, a dwell of about 15-120 minutes is introduced at a temperature of about 200 to about 250° C.

After calcination step (c), the resulting catalyst particles may be reduced at a temperature range of about 200 to about 500° C., in one embodiment from about 250 to about 350° C., in a reducing gas, preferably hydrogen.

The use of the catalyst of the present invention in the above alkylation process results in a high olefin conversion (amount of olefin in the feed that is converted in the reaction), a high C5+ alkylate yield (weight amount of C5+ alkylate produced divided by the overall weight of olefin consumed) and a high octane number, while the amount of in the case of this process desired C9+ by-products can be controlled and optimized.

General Test Procedure:

The proposed test procedure includes, a fixed-bed recycle reactor as described in WO 9823560, which is herein incorporated by reference in its entirety, having a diameter of 2 cm which is filled with a 1:1 volume/volume mixture of 38.6 grams of catalyst extrudates (on dry basis, LOI600) and carborundum particles (60 mesh). At the center of the reactor tube a thermocouple of 6 mm in diameter is arranged. The reactor is flushed with dry nitrogen for 30 minutes (21 Nl/hour). Next, the system is tested for leakages at elevated pressure, after which the pressure is set to 21 bar and the nitrogen flow to 21 Nl/hour. The reactor temperature is then raised to 275° C. at a rate of 1° C./min, at 275° C. nitrogen is replaced by dry hydrogen and the catalyst is reduced at 275° C.

Alternatively, in case of high temperature regeneration of the same catalyst sample between runs, after draining and flushing the reactor with hydrogen to remove hydrocarbons while maintaining the alkylation reaction temperature, hydrogen flow is set to 21 Nl/hour and the reactor temperature is then raised to 275° C. at a rate of 1° C./min, and the catalyst is regenerated at 275° C.

After 2 hours, the reactor temperature is lowered to the reaction temperature of about 55-85° C. During cooling down water is added to the hydrogen flow to obtain an water content of the catalyst of about 2-4 wt % (defined as the catalyst's water loss after heating for two hours at 600° C.).

The hydrogen stream is stopped with the attaining of the reaction temperature. Isobutane containing about 4 wt % alkylate (added to accelerate deactivation rate, composition of the alkylate added is similar to alkylate produced by the process at the conditions described) and about 1 mol % of dissolved hydrogen is supplied to the reactor at a rate of about 4.0 kg/hour. About 95-99% of the isobutane/alkylate mixture is fed back to the reactor. About 1-5% is drained off for analysis. Such an amount of isobutane/alkylate mixture is supplied to the reactor as to ensure a constant quantity of liquid in the system. When the system has stabilized, hydrogen addition is stopped and such an amount of cis-2-butene is added to it as to give a cis-2-butene-WHSV of 0.1-0.3. The overall rate of flow of liquid in the system is maintained at about 4.0 kg/h. The weight ratio of isobutane to cis-2-butene at the reactor inlet is about 250-1000. The pressure in the reactor amounts to about 21 bar. By variation of process conditions within the ranges above an alkylate product with varying C9+ content should be produced.

Each time after 1 hour of reaction, the catalyst is regenerated by being washed with isobutane/alkylate mixture for 5 minutes, followed by 50 minutes of regeneration through being contacted with a solution of 1 mole % of H2 in isobutane/alkylate mixture, and then being washed with isobutane/alkylate mixture for another 5 minutes (total washing and regeneration time 1 hour). After this washing step, alkylation is started again.

The temperature during the washing steps, the regeneration step, and the reaction step is the same. The process is conducted as above and the composition of products is measured by GC.

By GC analyses of the hydrocarbon compounds present in the C5+ alkylate (see e.g. WO 9823560 and more recently U.S. Pat. No. 8,163,969 B2) we would be able to calculate the weight % (wt %) of the various hydrocarbon compounds in the alkylate product mixture. After, we can calculate the RON of the total C5+ alkylate and the RON of the C5+ alkylate without the C9+ fraction. We define the heavier C9+ fraction as all components boiling from about 150° C. and higher, this includes n-nonane (nC9) and higher boiling C9+ components. So the final boiling point (FBP) of the gasoline fraction after separation of heavier C9+ alkylate will be maximum about 150° C., which makes it a very useful gasoline blending component. Similarly, the total C9+ fraction is calculated as all components boiling from about 124° C., the boiling point of 2,2,5-trimethylpentane, which is the C9 compound with the lowest boiling point present in significant amounts.

Relative high amounts of C9+ can be produced and after separation a gasoline alkylate will remain which has a very high RON of over 95, preferably over 96, more preferably over 97, notwithstanding that the alkylate is produced under relatively severe conditions that led to the high C9+ content.

In the case of the existing processes the RON of the gasoline alkylate fraction was much lower, i.e. about 95. In case of HF and $H_2SO_4$ processes the formation of ASO's that accompanies the kerosene formation will lead to waste formation and less favorable product composition and properties.

EXAMPLES

A catalyst of the present invention was made according to the description contained herein and in accordance with Patent Application WO 2016/005391, which is incorporated herein by reference. Specifically, a catalyst comprising RE exchanged and steamed Y-zeolite, alumina and Pt was used. It was then tested as described above. Results of the test are presented in table 1.

Table 1 displays the effect of process conditions on the product distribution of the C5+ alkylate. Both total C9+ and heavier C9+ fractions are reported. Cut>nC9 shows the effect of separating all components that have a boiling point above nC9 including nC9 from the alkylate. Cut>225TMH shows the effect of separating all components that have a boiling point above 2,2,5-trimethylhexane (225TMH) including 225TMH from the alkylate.

Olefin conversion is the conversion of olefin feed to mainly C5+ alkylate next to traces of n-butane. RON is calculated as described in the General Test Procedure from the GC data. It can be observed that at lower I/O and higher whsv more of the C9+ and heavier C9+ compounds are formed resulting in lower RON of the alkylate. Depending on the severity of the process conditions and the extent of separation of the C9+ fractions, RON increases with about 0.7 to about 1.8 point. For comparison also typical gasoline alkylate process conditions and resulting properties are presented.

TABLE 1

|  |  |  | 1 | 2 | 3 | 3 | 5 | 6 | Typical Gasoline |
|---|---|---|---|---|---|---|---|---|---|
| Conditions | | | | | | | | | |
| Temp | | [° C.] | 75 | 75 | 75 | 75 | 75 | 75 | 75 |
| I/O ext | | | 24-26 | 20-22 | 18-19 | 12-14 | 10-12 | 8-10 | 14-15 |
| WHSV | | | 0.10 | 0.12 | 0.18 | 0.19 | 0.19 | 0.19 | 0.16 |
| Olefin conversion | | [%] | 100.0 | 100.0 | 99.9 | 99.7 | 99.3 | 98.6 | 99.9 |
| Alkylate product | | | | | | | | | |
| FBP <150° C. | C5-nC9 | [wt %] | 94.4 | 93.7 | 91.0 | 89.9 | 88.9 | 87.2 | 91.5 |
| FBP >150° C. | sum nC9+ | [wt %] | 5.6 | 6.2 | 9.0 | 10.0 | 11.0 | 12.6 | 8.5 |
| Compounds | C5-C8 | [wt %] | 91.6 | 90.7 | 87.2 | 85.5 | 84.5 | 82.2 | 88.2 |
| Total compounds | C9+ | [wt %] | 8.4 | 9.2 | 12.7 | 14.4 | 15.3 | 17.5 | 11.8 |
| | RON | | 96.2 | 96.0 | 95.8 | 95.4 | 95.2 | 95.0 | 95.5 |
| Alkylate cut > nC9 | | | | | | | | | |
| FBP <150° C. | C5-nC9 | [wt %] | 100.0 | 100.0 | 100.0 | 100.0 | 100.0 | 100.0 | |
| FBP >150° C. | sum nC9+ | [wt %] | 0.0 | 0.0 | 0.0 | 0.0 | 0.0 | 0.0 | |
| Compounds | C5-C8 | [wt %] | 97.0 | 96.8 | 95.9 | 95.1 | 95.1 | 94.3 | |
| Compounds | 225TMH-nC9 | [wt %] | 3.0 | 3.2 | 4.1 | 4.9 | 4.9 | 5.7 | |
| | RON | | 96.9 | 96.8 | 96.6 | 96.5 | 96.4 | 96.3 | |
| Alkylate cut >225TMH | | | | | | | | | |
| Compounds | C5-C8 | [wt %] | 100.0 | 100.0 | 100.0 | 100.0 | 100.0 | 100.0 | |
| Total compounds | 225TMH-nC9 | [wt %] | 0.0 | 0.0 | 0.0 | 0.0 | 0.0 | 0.0 | |
| | RON | | 97.1 | 97.0 | 96.9 | 96.9 | 96.8 | 96.8 | |

The invention claimed is:

1. A process for alkylating hydrocarbons for producing a gasoline alkylate quantity wherein a feed comprising alkylatable organic compound, comprising an isoparaffin or mixture of isoparaffins, is reacted with an alkylation agent, comprising n-butene or a mixture of butenes, to form an alkylate in the presence of a catalyst at a temperature between 75° C. and 95° C., wherein said catalyst comprises a hydrogenating function, a solid acid constituent, and one or more rare earth elements; wherein the feed is processed using process conditions that lead to a higher quantity of a C9+ product fraction formed than process conditions optimized for gasoline production, wherein the quantity of co-produced C9+ product fraction is higher than 11 wt % by weight of the gasoline alkylate quantity produced, including condition a) and/or b):
   a) wherein the feed is processed at WHSV of the olefin at greater than 100% of the WHSV for gasoline production only;
   b) wherein I/O external is less than 100% of an I/O external for gasoline production.

2. A process according to claim 1 comprising a further step of separation of the C9+ product fraction produced by the process.

3. A process according to claim 2 comprising wherein the step of separation is done by distillation.

4. A process according to claim 1 further comprising a step of distilling a gasoline fraction.

5. A process according to claim 3, wherein a gasoline fraction after distillation has a RON greater than 94 and is essentially free of nitrogen and/or sulfur.

6. A process according to claim 3, wherein a gasoline fraction after distillation has a RON greater than 95.

7. A process according to claim 3, wherein a gasoline fraction after distillation has a RON greater than 96.

8. A process according to claim 1, wherein the feed is processed at WHSV of the alkylation agent at greater than 110% of the WHSV for gasoline production only.

9. A process according to claim 1, wherein the feed is processed at WHSV of the alkylation agent at greater than 100% but less than 150% of the WHSV for gasoline production only.

10. A process according to claim 1, wherein I/O external is from about 50% to 100% of an I/O external for gasoline production.

11. A process according to claim 1, wherein the one or more rare earth elements comprises cerium.

12. A process according to claim 11, wherein the one or more rare earth elements comprise at least 0.1 wt % cerium, calculated as fraction of the total catalyst weight.

13. A process according to claim 12, wherein the one or more rare earth elements comprise at least 0.3 wt % cerium, calculated as fraction of the total catalyst weight.

14. A process according to claim 1, wherein the one or more rare earth elements are comprised of cerium and lanthanum.

15. The process of claim 1 wherein the alkylatable organic compound is isobutane.

16. The process of claim 1 wherein the catalyst is prepared by a) calcining solid acid-containing particles at a temperature in the range of 400-575° C., b) incorporating a Group VIII metal into the calcined particles to form metal-containing particles, and c) calcining the metal-containing particles at a temperature in the range of 350-600° C.

17. The process of claim 16 wherein the Group VIII metal is a noble metal.

18. A process according to claim 17 wherein the temperature applied in step a) is in the range of 450-550° C.

19. A process according to claim 16 wherein the temperature applied in step a) is in the range of 450-550° C.

20. A process according to claim 19 wherein the temperature is in the range of 460-500° C.

21. The process according to claim 1 wherein the catalyst further comprises from about 1.5 to about 6 wt % of water (LOI600).

\* \* \* \* \*